United States Patent [19]

Taylor

[11] Patent Number: 4,510,294

[45] Date of Patent: Apr. 9, 1985

[54] POLYMERIZATION OF MONOMERIC HYDROGEN-BLOCKED OXIME DERIVATIVES

[75] Inventor: Lloyd D. Taylor, Lexington, Mass.

[73] Assignee: Polaroid Corporation, Cambridge, Mass.

[21] Appl. No.: 394,543

[22] Filed: Jul. 2, 1982

[51] Int. Cl.$^3$ ................................................ C08F 8/12
[52] U.S. Cl. ..................................... 525/369; 525/355; 525/359.4; 526/288; 526/304
[58] Field of Search ............... 525/344, 355, 369, 378, 525/386, 359.4, 328.2, 328.4, 329.4

[56] References Cited

U.S. PATENT DOCUMENTS

| | | | |
|---|---|---|---|
| 3,268,480 | 8/1966 | Wagenaar | 430/215 |
| 4,202,694 | 5/1980 | Taylor | 430/215 |
| 4,256,614 | 3/1981 | Taylor | 525/369 |

OTHER PUBLICATIONS

Hong, S. I. et al., J. of Polym. Science: Polymer Chem. Ed., vol. 12, 1974, pp. 2553–2566.
Masuda, S. et al., Polymer Journal, vol. 11, No. 8, pp. 641–649 (1979).
Masuda, Polymer Journal, vol. II, No. 3, pp. 213–218 (1979).
Masuda, Polymer Journal, vol. 10, No. 4, pp. 387–395 (1978).
Zaitsev, B. A. et al., Vysokomol., Soyed., A10: No. 2, 434–445 (1968).

*Primary Examiner*—Christopher A. Henderson
*Attorney, Agent, or Firm*—Louis G. Xiarhos

[57] ABSTRACT

A process for preparing high molecular weight polymeric oximes is disclosed which comprises providing a hydrogen-blocked derivative of an ethylenically unsaturated monomeric oxime; effecting the polymerization of the monomeric hydrogen-blocked oxime derivative; and removing the blocking groups from the recurring units of the resulting polymer and replacing the blocking groups with hydrogen atoms, thereby providing a polymeric oxime.

17 Claims, No Drawings

POLYMERIZATION OF MONOMERIC HYDROGEN-BLOCKED OXIME DERIVATIVES

BACKGROUND OF THE INVENTION

This invention relates to a process for preparing polymeric oximes. More particularly, it relates to certain hydrogen-protected monomeric oxime derivatives and to the production of polymeric oximes therefrom.

Polymeric oximes which may be characterized as polymers including an oximino group of the formula >C=N—OH are known and are described, for example, in U.S. Pat. No. 3,268,480 (issued Aug. 23, 1966 to A. H. Wagernaar et al.) and in U.S. Pat. No. 4,202,694 (issued May 13, 1980 to L. D. Taylor). In general, polymeric oximes are prepared by first preparing a polymer of a polymerizable monomeric compound containing at least one carbonyl (>C=O) group and, then, oximating the polymer with hydroxylamine reagent so as to convert carbonyl groups to oximino groups.

The preparation of certain polymeric oximes by the method of polymerizing a monomeric oxime has also been reported. In a series of publications by Masuda et al., in Polymer Journal, Vol. 11, No. 8, pp. 641–649 (1979); Vol. 11, No. 3, pp. 213–218 (1979); Vol. 10, No. 4, pp. 397–402 (1978); and in publications referenced therein, there is described the polymerization of acrolein oxime in organic solvent systems employing various means of initiating the polymerization reaction. The molecular weights of the polymers obtained were reported to be very low, generally about 1000 to 3000. The copolymerization of p-vinylacetophenone oxime with styrene and methylmethacrylate and p-isopropenylacetophenone oxime with styrene using ethyl alcohol or alcohol-benzene as a solvent is reported by B. A. Zaitsev and G. A. Shtraikhman in Vysokomol. soyed., A10: No. 2, 434–445 (1968), English translation at page 511. Molecular weights of the resulting polymers are not reported. In the aforementioned U.S. Pat. No. 4,202,694, reference is made to certain unsuccessful attempts to prepare high molecular weight polymers by polymerization of a monomeric oxime.

Owing to an apparent tendency of the oximino group of an ethylenically unsaturated monomeric oxime to exert an inhibiting effect upon the polymerization of the monomeric oxime and the resulting production, in general, of low molecular weight polymers, resort is made to the aforementioned method whereby a polymer is first prepared from a polymerizable monomer containing a carbonyl group and the resulting polymer is, then, subjected to an oximation procedure. This method may, however, impose limitations on the production of certain polymeric oximes. For example, it is oftentimes desirable to introduce water-solubilizing groups or other specific functionality into a polymeric oxime. Thus, copolymers of the carbonyl-containing monomer and a copolymerizable monomer will be prepared and then subjected to oximation conditions which may exert a hydrolytic or other adverse effect upon the recurring units introduced by the copolymerizable monomer. Moreover, the completeness of conversion of carbonyl-to-oximino groups can vary with the nature of the oximation conditions and the polymer such that it may be desirable to provide oximino groups in a polymer in controlled manner and as a function of a polymerizable oxime monomer.

SUMMARY OF THE INVENTION

According to the present invention, there is provided a process for preparing high molecular weight polymeric oximes from a polymerizable derivative of an ethylenically unsaturated monomeric oxime. The process of this invention comprises providing a polymerizable hydrogen-blocked derivative of an ethylenically unsaturated monomeric oxime, said oxime derivative having the formula

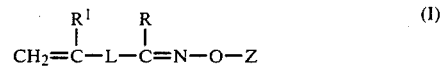

wherein R is hydrogen, lower alkyl, aryl, aralkyl or alkaryl, $R^1$ is hydrogen or lower alkyl, L is a divalent organic linking group and Z is a hydrogen-blocking group capable of being replaced by a hydrogen atom; effecting the polymerization of the hydrogen-blocked oxime derivative, thereby to provide a polymer comprising recurring units from said polymerizable hydrogen-blocked oxime derivative; and replacing hydrogen-blocking Z groups of said polymer with hydrogen atoms, thereby to provide a polymer containing oximino groups.

According to a preferred aspect of this invention, the polymerizable hydrogen-blocked derivative is an aldoxime- or ketoxime-derivative of the formula

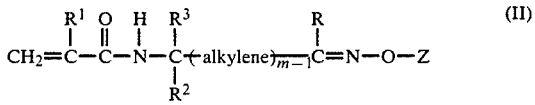

wherein R, $R^1$ and Z are as previously defined, each of $R^2$ and $R^3$ is independently lower alkyl having from 1 to 6 carbon atoms, the alkylene moiety has from 1 to 8 carbon atoms, and m is an integer of one or two.

The high molecular weight polymeric oximes prepared by the process of the present invention can be employed, for example, as viscosity-increasing reagents in aqueous alkaline photographic processing compositions.

For a fuller understanding of the present invention, reference should be had to the following detailed description.

DETAILED DESCRIPTION OF THE INVENTION

The present invention relates to a process whereby hydrogen-blocked derivatives of monomeric ketoximes and aldoximes are employed to prepare high molecular weight polymeric ketoximes and aldoximes, i.e. high molecular weight polymers having ketoxime or aldoxime moieties pendant to the polymer backbone. For purposes of brevity and convenience, the hydrogen-blocked monomeric ketoxime and aldoxime derivatives employed in this invention are hereinafter referred to simply as monomeric oxime derivatives. Similarly, the polymeric ketoximes and aldoximes produced in accordance with the present invention are hereinafter referred to simply as polymeric oximes.

The process of the present invention involves the utilization of polymerizable ethylenically unsaturated hydrogen-blocked derivatives of monomeric oximes.

These derivatives are polymerizable monomers of the formula

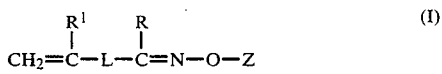 (I)

wherein R is hydrogen, lower alkyl, e.g., methyl, ethyl, isopropyl; aryl, e.g., phenyl; alkaryl, e.g., tolyl; or aralkyl, e.g., benzyl; $R^1$ is hydrogen or lower alkyl, e.g., methyl, ethyl, isopropyl; L is a divalent organic linking group; and Z is a hydrogen-blocking group capable of being replaced by a hydrogen atom. It will be appreciated from inspection of the monomeric oxime derivatives of formula (I) that monomeric aldoxime derivatives are contemplated where R is hydrogen and that the derivatives are ketoxime derivatives when R is as otherwise defined. The derivatives of formula (I) are provided by derivatization of corresponding monomeric oximes such that hydrogen-blocking groups, Z, are introduced in place of hydrogen atoms of the oxime monomers of the formula

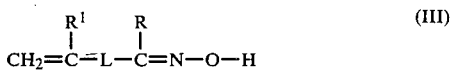 (III)

wherein R, $R^1$ and L have the meanings previously defined.

The nature of the hydrogen-blocking Z group of the monomeric derivative of formula (I) can vary provided that the oxime derivative will undergo ethylenic polymerization and the blocking group of the resulting polymer can be replaced with a hydrogen atom for production of a polymeric oxime. Depending upon the particular hydrogen-blocking Z group, the polymerizable oxime derivative can be, for example, a carbonate derivative, a carbamate derivative or an ether or ester derivative or the like.

Suitable Z blocking groups include hydrogen-blocking groups

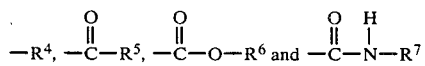

where each of $R^4$, $R^5$, $R^6$ and $R^7$ is independently alkyl (e.g., methyl, ethyl, n-propyl, isopropyl, n-hexyl), aryl (e.g., phenyl), alkaryl (e.g., tolyl), aralkyl (e.g., benzyl), a carbocyclic radical (e.g., cyclohexyl) or a 5- or 6-membered heterocyclic radical (e.g., tetrahydrofuranyl, tetrahydropyranyl).

Other suitable hydrogen-blocking Z groups include

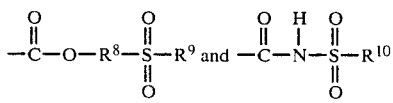

where $R^8$ is a divalent alkylene or arylene radical (e.g., methylene, ethylene or p-phenylene) and each of $R^9$ and $R^{10}$ is independently alkyl (e.g., methyl, ethyl), aryl (e.g., phenyl), alkaryl (e.g., tolyl), aralkyl (e.g., benzyl), a carbocyclic radical (e.g., cyclohexyl) or a 5- or 6-membered heterocyclic radical (e.g., tetrahydrofuranyl, tetrahydropyranyl). The $R^4$, $R^5$, $R^6$, $R^7$, $R^8$, $R^9$ and $R^{10}$ radicals can contain substituent atoms provided that the substituents do not inhibit polymerization of the hydrogen-blocked oxime derivative or interfere with desired deblocking of the derivative for production of a polymeric oxime. Suitable substituted radicals include, for example, trifluoromethyl, nitrophenyl, phenacyl, perfluoroacyl and the like.

It will be appreciated that other hydrogen-blocking groups can be employed for the provision of oxime derivatives capable of being polymerized to high molecular weight polymers and that the blocking groups specifically recited are set forth by way of example. Preferred blocking groups are the aforesaid

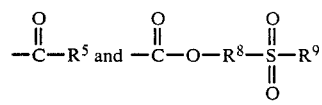

hydrogen-blocking groups wherein $R^5$, $R^8$ and $R^9$ have the meanings aforedescribed. These hydrogen-blocking groups permit the production of a polymer which can be subjected to a hydrolysis treatment under mildly acidic or alkaline conditions for production of the desired and corresponding polymeric oxime.

A polymerizable ester derivative of an ethylenically unsaturated monomeric oxime can be provided by reaction of a monomeric oxime of the formula (III) with a halide of the formula

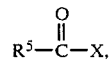

where X is chloro or bromo and $R^5$ has the meaning previously defined, or with an anhydride of the formula

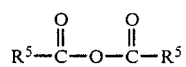

where each $R^5$ has the meaning previously defined. The production of an ester derivative of an oxime of formula (III) is illustrated by the following reaction scheme in which is shown the reaction of a monomeric oxime of formula (III) with acetic anhydride to provide the acetyl derivative

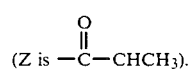

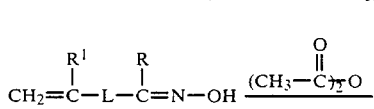

A polymerizable ether derivative of an oxime of formula (III) can be suitably provided by reacting the oxime with a halide of the formula $R^4$-X, where X is chloro or bromo and $R^4$ has the meaning aforedescribed. Formation of an ether derivative (where Z is

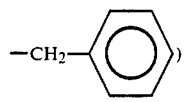

is illustrated in the following reaction scheme in which a monomeric oxime of formula (III) is shown reacted with benzyl bromide.

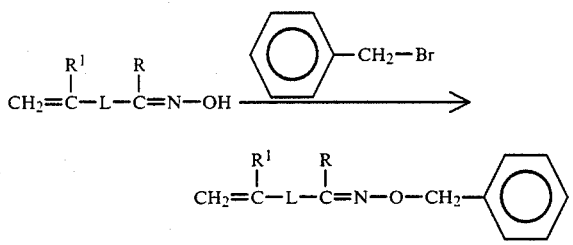

Polymerizable carbamate derivatives can be provided by reaction of an oxime of formula (III) with an isocyanate having the formula

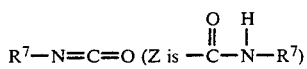

or with an isocyanate of the formula

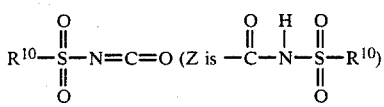

where $R^7$ and $R^{10}$ are as previously defined. This reaction is illustrated in the following reaction scheme which shows the reaction of the oxime with phenylisocyanate:

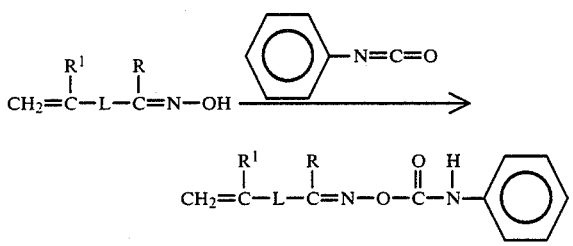

Polymerizable carbonate derivatives can be provided by reaction of an oxime of formula (III) with a haloformic acid ester of the formula

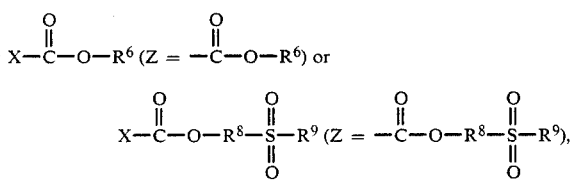

where X is halo, e.g., chloro or bromo, and $R^8$ and $R^9$ are as previously defined. This reaction is illustrated in the following reaction sequence showing the derivatization utilizing ethyl chloroformate:

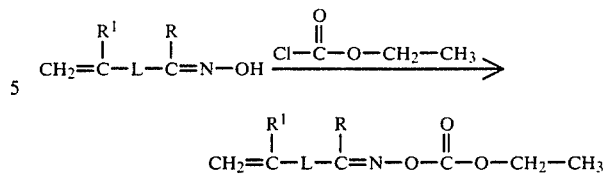

Polymerizable hydrogen-blocked derivatives of ethylenically unsaturated oximes can be provided from a variety of monomeric oximes of formula (III). In the hydrogen-blocked derivatives of formula (I), i.e., the hydrogen-blocked derivatives having the formula

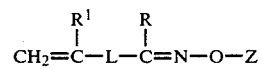

the L linking group will be a divalent organic group which is stable under the conditions of the polymerization process and which does not deleteriously affect the conduct of the polymerization reaction. In addition, the linking group will be stable to the conditions of a subsequent deblocking reaction involving the removal of hydrogen-blocking Z groups and the substitution of hydrogen atoms therefor.

Linking group L can be suitably selected from arylene, preferably containing from 6 to 10 carbon atoms such as phenylene, naphthylene or the like; arylenealkylene wherein the point of attachment to the oxime moiety is at a site on the alkylene moiety to provide, e.g.,

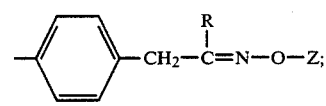

or the linking group

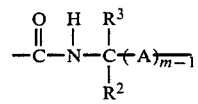

wherein each of $R^2$ and $R^3$ is independently hydrogen or lower alkyl having from 1 to 6 carbon atoms, A is alkylene, preferably containing from 1 to 8 carbon atoms, such as methylene, ethylene, isopropylene, and the like, arylene or arylenealkylene, and m is an integer 1 or 2.

Preferred hydrogen-blocked oxime derivatives for the production of polymeric oximes by the process hereof are those of formula (II) in which the linking group L is

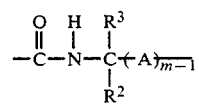

wherein each of $R^2$ and $R^3$ is independently lower alkyl of from 1 to 6 carbon atoms, m is an integer 1 or 2, and A is alkylene having from 1 to 8 carbon atoms such that the preferred hydrogen-blocked oxime derivatives will have the formula

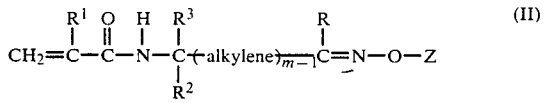

wherein R and $R^1$ and Z are as previously defined. In the oxime derivatives of formula (II), it will be preferred that $R^1$ be hydrogen or methyl; each of $R^2$ and $R^3$ be methyl or ethyl; alkylene be methylene, R be methyl; and m be the integer two.

As examples of polymerizable hydrogen-blocked derivatives of formula (I), mention may be made of the following oxime derivatives wherein Z has the meaning previously defined.

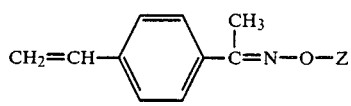

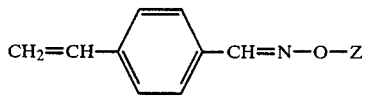

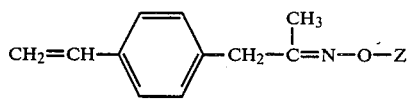

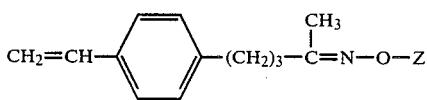

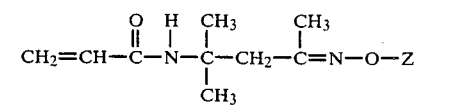

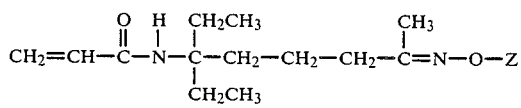

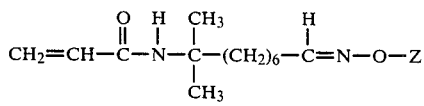

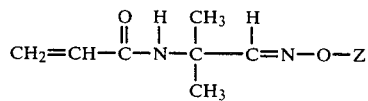

In the aforementioned examples of hydrogen-blocked oxime derivatives, the Z blocking group can vary as previously defined. Preferred Z groups include

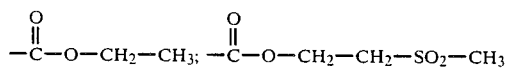

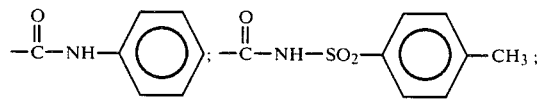

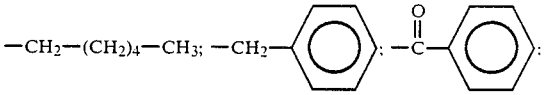

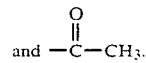

In general, the monomeric oximes employed as starting materials for the production of hydrogen-blocked derivatives can be prepared by reaction of the corresponding ketone or aldehyde precursor with hydroxylamine. The production of oximes by oximation of the corresponding ketone or aldehyde is a well known procedure which does not per se constitute a part of this invention.

The hydrogen-blocked oxime derivatives hereof can be readily polymerized to high molecular weight polymers which contain recurring units of the formula

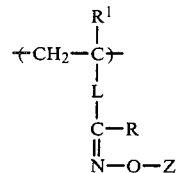

While applicant does not wish to be bound by any particular theory or mechanism in explanation of the polymerizable character of the hydrogen-blocked derivatives hereof, it is believed that the hydrogen-blocking Z groups in the monomeric derivatives permit desired polymerization to be effected by avoiding the polymerization-inhibiting effects of oxime groups. Polymerization of the hydrogen-blocked derivatives can, thus, be effected by resort to a variety of polymerization techniques to realize the production of high molecular weight derivatized polymers of certain nonpolymerizable monomeric oximes.

The hydrogen-blocked monomeric oxime derivatives can be polymerized into homopolymers or copolymers including graft polymers. These polymers can be suitably prepared, for example, by resort to solution polymerization or emulsion polymerization techniques or by use of methods employed for the preparation of graft copolymers. It will be appreciated that the particular polymerization procedure utilized will vary with the particular nature of the hydrogen-blocked oxime derivative and the solubility properties thereof in the particular solvent that may be employed. For example, an organic solvent such as dimethylformamide, benzene, dimethylsulfoxide or the like can be utilized as a solution polymerization medium for a redox or free-radical initiated polymerization.

In general, a hydrogen-blocked oxime derivative hereof will be introduced into a suitable solvent or other polymerization medium in the presence of a polymerization initiating agent. The polymerization is generally effected by introducing the initiating agent into the polymerization medium containing the oxime derivative and maintaining the polymerization medium under conditions of time and temperature sufficient to permit formation of the desired polymers. Temperatures within the range of about 0° C. to about 70° C. may, for example, be utilized in the polymerization reaction.

although optimum reaction temperatures will depend on such factors as the amount and type of polymerization initiating agent, the particular monomeric oxime derivative employed, and the solubility of the oxime derivative. In general, where an aqueous polymerization medium is utilized, it will be preferred to conduct the polymerization at a temperature of less than about 45° C. so as to minimize any hydrolysis of the hydrogen-blocked oxime derivative to the corresponding oxime so as to avoid polymerization-inhibiting effects.

A variety of polymerization initiating agents can be suitably employed to initiate or catalyze the polymerization reaction of this invention. The initiating agent should be soluble in the polymerization medium at least to an extent sufficient to permit the initiation and maintenance of the polymerization reaction. Preferred initiating agents are the redox initiators, i.e., polymerization initiators comprising a combination of an oxidizing agent and a reducing agent which is capable of reaction with the oxidizing agent. Redox combinations suitable for use as polymerization initiators are well known in the art. Reference may be had, for example, to the publication of R. G. R. Bacon, Trans. Faraday Soc., 42, 140 (1946) wherein is described a variety of oxidizing and reducing agents suitable for employment in redox initiating combinations. Oxidizing agents which may be employed in such redox initiating combinations include peroxides, such as hydrogen peroxide, and alkali persulfates such as ammonium persulfate, potassium persulfate, and sodium persulfate. Reducing agents which may be employed in the practice of this invention include salts, particularly sulfate salts, comprising a metal cation capable of undergoing oxidation, e.g., cuprous sulfate, ferrous sulfate, and hydrates thereof. Other reducing agents which may be employed include ascorbic acid and the various sulfites; bisulfites; metabisulfites; hydrosulfites; sulphoxylates; and thiosulfates. Good results can be obtained, for example, from a combination of sodium thiosulfate and sodium bisulfite. Good results can also be obtained using an azo-type initiator such as azobisisobutryronitrile.

In general, the present invention may be practiced employing less than about 5% by weight of initiating agent, based on the weight of starting monomer(s). The particular amount and concentration of initiating agent can depend, for example, on the efficiency of the agent, the particular monomeric oxime derivative employed, and the intended molecular weight of the product polymer. Generally, the minimum weight of initiating agent which is sufficient to sustain the reaction (usually less than 1% by weight based on the weight of starting monomer(s)) will be preferred, such minimum amount of initiating agent generally tending to promote formation of higher molecular weight polymers.

As mentioned previously, the hydrogen-blocked oxime derivatives hereof can be employed for the production of homopolymers or copolymers. Copolymers can be suitably prepared by the copolymerization of a monomeric hydrogen-blocked derivative of formula (I) with another copolymerizable monomer(s). Comonomers which can be utilized for the production of such copolymers include such copolymerizable ethylenically unsaturated comonomers as the N-alkylacrylamides, N,N-dialkylacrylamides, alkylacrylates, alkylmethacrylates, vinyl acetate, diacetone-acrylamide, 2-acrylamido-2-methylpropane sulfonic acid, acrylic acid and methacrylic acid. If desired, copolymers can be prepared by the copolymerization of two or more copolymerizable monomeric hydrogen-blocked oxime derivatives of formula (I) wherein the monomers have, for example, different linking groups, L, or different hydrogen-blocking groups, Z.

It will be appreciated that the particular nature of the copoymerizable monomers utilized in the copolymerization reaction will materially influence the properties of the resulting copolymer and the corresponding oxime polymer produced by the replacement of Z blocking groups with hydrogen atoms. Thus, depending upon the particular application contemplated for a copolymer prepared by the process hereof, a polymerizable comonomer can be employed to introduce hydrophobicity, water-solubilizing or other functionality. For example, a copolymer of a hydrogen-blocked derivative of diacetone acrylamide oxime and acrylic acid can be prepared and hydrolyzed for the production of poly(-diacetoneacrylamide-oxime-co-acrylic acid) which can be suitably employed as a viscosity-increasing agent in aqueous alkaline photographic processing compositions. The utilization of polymeric oximes including poly(diacetoneacrylamide oxime-co-acrylic acid) as viscosity-increasing agents in photographic processing compositions is disclosed in the aforecited U.S. Pat. No. 4,202,694.

The process of the present invention permits the realization of certain advantages over the production of polymeric oximes by the oximation of a polymeric ketone or aldehyde. For example, oxime content of a polymeric oxime can be controlled in predetermined manner by forming a copolymer of diacetone acrylamide and a hydrogen-blocked derivative of the oxime thereof and hydrolyzing the product to poly(diacetone acrylamide-co-diacetone acrylamide oxime) as is illustrated in the following reaction scheme wherein a and b represent molar proportions of the respective recurring units:

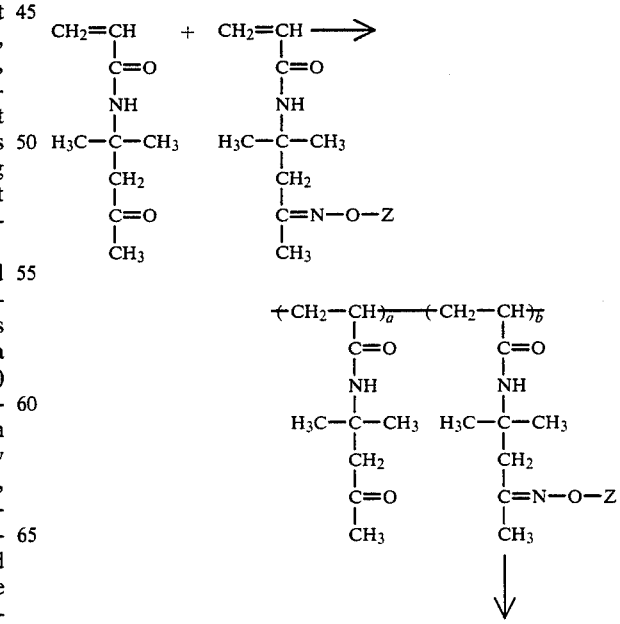

-continued

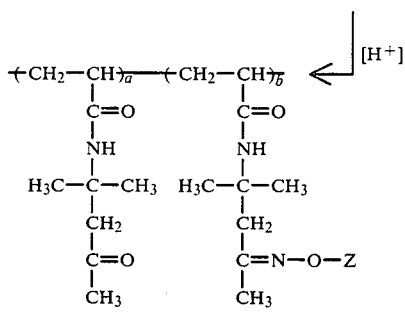

The process of the invention also permits the production of copolymers of a blocked oxime and an ethlenically unsaturated comonomer that may be unstable to highly alkaline oximation condition, e.g., an alkyl acrylate such as butyl acrylate. By the process of the present invention, a copolymer of an alkyl acrylate and a hydrogen-blocked diacetone acrylamide oxime derivative can be prepared and the resulting polymer can be deblocked to provide poly(diacetone acrylamide oxime-co-alkyl acrylate).

Polymeric oximes can be prepared from the polymeric hydrogen-blocked oxime derivatives by a deblocking procedure by which Z blocking groups are replaced with hydrogen atoms. In general, the polymeric hydrogen-blocked oxime derivative will be deblocked by resort to a hydrolysis procedure and mechanism. The hydrolysis can be effected under acidic, neutral or alkaline conditions depending upon the particular blocking groups present in the polymer derivative. For example, where the blocking group is a group of the formula

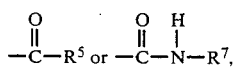

as previously defined, production of the corresponding polymeric oxime can be effected under alkaline hydrolytic conditions, e.g., aqueous sodium hydroxide or potassium hydroxide. Hydrogen-blocking groups, Z, capable of removal under acidic conditions, e.g., trifluoroacetic acid or dilute aqueous hydrochloric acid, include tetrahydrofuranyl, tetrahydropyranyl and phenacyl. The deblocking of a polymeric hydrogen-blocked oxime derivative is illustrated in the following reaction scheme which illustrates the replacement of tetrahydrofuranyl derivatizing groups of polymeric diacetone acrylamide oxime with hydrogen atoms using dilute aqueous hydrochloric hydrolysis:

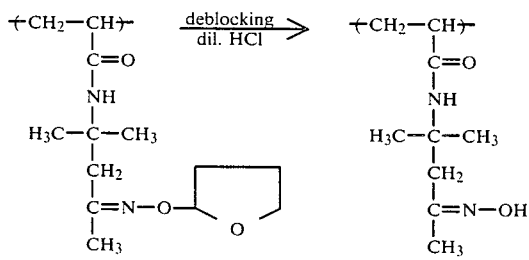

The following Examples are provided to further illustrate the present invention and are not intended to be of limiting effect.

EXAMPLE 1

Part A

Preparation of the N-phenyl carbamate derivative of diacetone acrylamide oxime

A solution of 3.88 grams (0.0325 mole) of phenyl isocyanate was added dropwise over a 15-minute period to a stirred solution of 6 grams of diacetone acrylamide oxime (0.0325 mole) and two drops of triethylamine in 24 grams of tetrahydrofuran at 26° C. The reaction temperature elevated to a 37° C. exotherm, and upon completion of the addition, the reaction contents were heated for one hour at 40° C. Upon cooling, 200 mls. of diethyl ether were added and the reaction mixture was chilled in a refrigerator with formation, in 88% yield, of a white crystalline product. The product was recrystallized from ethyl acetate and showed a melting point of 157°–158° C. The following structure was confirmed by thin layer chromatographic and nuclear magnetic resonance techniques:

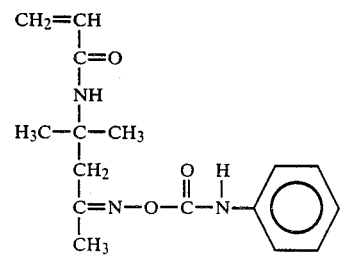

Part B

Polymerization of the N-phenyl carbamate derivative of diacetone acrylamide oxime Five grams of the N-phenyl carbamate derivative of diacetone acrylamide oxime, prepared as described in Part A of this Example, were dissolved in a polymerization tube containing 20 mls. of dimethylformamide that had been dried using 4 A zeolitic molecular sieves. The contents of the polymerization tube were purged with nitrogen for 16 hours. A polymerization initiator (0.01 gram of azobisisobutyronitrile) was added and the polymerization tube was sealed under vacuum. The resulting solution was maintained in the sealed tube at 65° C. for 40 hours. Upon completion of polymerization, the contents of the polymerization were added dropwise to a vessel containing stirred diethyl ether. Formation of a white polymeric product was observed. The product exhibited solubility in tetrahydrofuran and in ethyl acetate. Coating of a solution of the polymer onto a glass slide showed the polymer to be film-forming.

EXAMPLE 2

Part A

Preparation of the benzoate ester derivative of diacetone acrylamide oxime

In a reaction vessel equipped with a reflux condenser, a reaction mixture of benzoic anhydride (11.3 grams; 0.05 mole), diacetone acrylamide oxime (9.2 grams; 0.05 mole) and diethyl ether (50 mls.) was heated at reflux for 30 minutes to provide a clear solution. Another 50 mls. of diethyl ether were added and the ether phase of the reaction contents was extracted with three 50-ml. portions of 10% aqueous potassium bicarbonate solution, followed by extraction with 20 mls. of water. After drying the ether solution over a mixture of calcium sulfate drying agent (Drierite) and powdered potassium bicarbonate, the solvent was evaporated and a white solid residue was recrystallized from a benzene/hexane mixture to yield 7.9 grams (55% yield) of a white crystalline product showing a melting point of 115°–118° C. Analysis for $C_{16}H_{20}N_2O_3$ provided the following:

Calculated: C, 66.4; H, 6.9; N, 10.0. Found: C, 66.0; H, 7.0; N, 9.7.

The following structure was confirmed by infrared analysis:

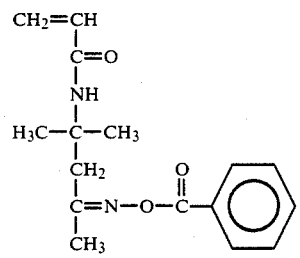

Part B

Polymerization of the benzoate ester derivative of diacetone acrylamide oxime

A solution of 2.0 grams of recrystallized benzoate ester of diacetone acrylamide oxime (prepared as described in Part A of this Example), 15 mls. of benzene and 0.005 gram of azobisisobutyronitrile was heated overnight at 65° C. in a sealed tube. The polymerization reaction yielded a clear viscous liquid. The polymer (1.8 grams) was recovered by adding the viscous liquid dropwise to a vessel containing stirred diethyl ether. The polymer was recovered by filtering the reaction product, washing with diethyl ether and drying in a vacuum oven. The resulting polymer was soluble in benzene, ethanol, acetone and ethylacetate. A solution of the polymer coated onto a glass slide showed the polymer to be film-forming.

EXAMPLE 3

Part A

Preparation of the methylsulfonylethyl derivative of diacetone acrylamide oxime

A solution was prepared from 12.7 grams (0.068 mole) of methylsulfonylethyl chloroformate (freshly crystallized from tetrahydrofuran) and 250 mls. of methylene chloride and the solution was stirred at high speed in a Waring blender with about 100 grams of ice. An aqueous solution of the potassium salt of diacetone acrylamide oxime was prepared from 11.4 grams (0.0619 mole) diacetone acrylamide oxime, 3.30 grams potassium hydroxide (0.589 mole) and 250 mls. water and was added dropwise at room temperature over a 15-minute period to the vortex created by the high-speed blending. After ten additional minutes of stirring, solid sodium chloride was added portionwise to the reaction mixture. The resulting dispersion was then separated using a separatory funnel and the aqueous layer was repeatedly extracted using dichloromethane. Combined organic layers were dried at low temperature using anhydrous sodium sulfate. Solvent was stripped at reduced pressure at a temperature below 45° C. The resulting pale oil was triturated with hexane to provide a chalk-white solid (56% yield). Recrystallization from benzene provided 11.6 grams of pure product having a melting point of 86°–87° C.

Combustion analysis of three samples of product provided the following results:

|  | % C | % H | % N | % S |
|---|---|---|---|---|
| Calculated: | 46.69 | 6.63 | 8.38 | 9.59 |
| Found: | 46.80 | 6.81 | 8.32 | 9.97 |
|  | 46.90 | 6.81 | 8.29 | 9.80 |
|  | 47.04 | 6.77 | 8.34 | 9.81 |

Resort to proton NMR and C13 NMR analytical techniques confirmed the production of the following Z and E monomeric forms at weight percentages, respectively, of 98.6 and 1.4.

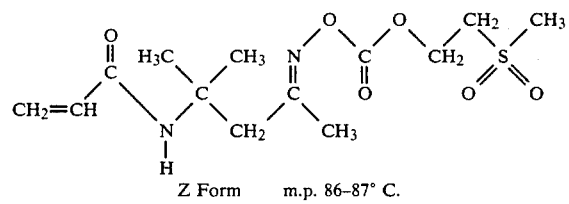

Z Form    m.p. 86–87° C.

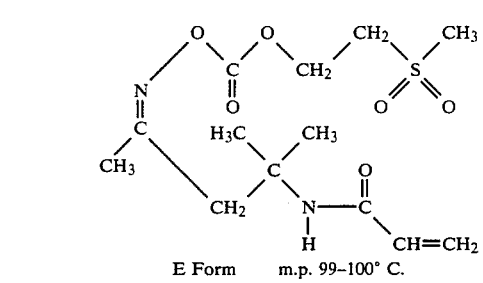

E Form    m.p. 99–100° C.

Part B

Polymerization of the methylsulfonylethyl derivative of diacetone acrylamide oxime A 6.7% (by wt.) solution of the monomer prepared as described in Part A of this Example was polymerized at room temperature under nitrogen using 2% by weight of a redox initiator (potassium thiosulfate and sodium bisulfite at a 72/28 weight ratio). The onset of polymerization was noted six minutes after addition of the initiators to the monomer solution. After 16 hours, conversion was 65%. Water insoluble polymer was filtered off, washed and dried. The polymer was soluble in acetonitrile, dimethylformamide and dimethyl sulfoxide.

EXAMPLE 4

Preparation of the ethyl carbonate derivative of diacetone acrylamide oxime

A solution of diacetone acrylamide oxime (12.46 grams; 0.0676 mole) and ethyl chloroformate (8.14 grams; 0.075 mole) in methyl cyanide was stirred under anhydrous conditions at 58° C. for 18 hours in the presence of proton sponge, 1,8-bis(dimethylamino)naphthalene (14.5 grams; 0.0676 mole). Salts formed during the reaction were filtered off and the filtrates were stripped under reduced pressure to provide an amber oil. Trituration of the oil with tetrahydrofuran produced a second portion of salts. Tetrahydrofuran filtrates were concentrated to a small volume from which the desired product crystallized. One recrystallization from tetrahydrofuran provided the desired polymer in an amount of 8.66 grams (50% yield) having a melting point of 74°–75° C.

Combustion analysis of two samples provided the following results:

|  | % C | % H | % N |
|---|---|---|---|
| Calculated: | 56.23 | 7.86 | 10.93 |
| Found: | 56.28 | 7.61 | 10.83 |
|  | 56.38 | 7.68 | 10.88 |

Resort to proton NMR and C13 NMR analytical techniques confirmed the following structure:

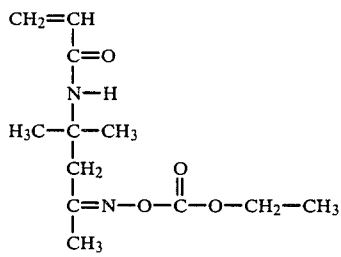

EXAMPLE 5

Preparation of the hexyl ether derivative of diacetone acrylamide oxime n-Hexyl bromide (22.4 grams; 0.136 mole) and diacetone acrylamide oxime (25 grams; 0.136 mole) were dissolved in 200 mls. of dimethylformamide that had been dried over molecular sieves. Potassium hydroxide pellets (9.15 grams; 0.163 mole) were added to the solution at 65° C. Within one half hour, the pellets dissolved and a white solid appeared. After holding the reaction mixture at 65° C. for 1.5 hours, a pink waxy solid was precipitated by pouring the reaction mixture in 1.5 liters of ice water. The product was filtered off and the resulting crude material was precipitated from ethanol with ice water, which, when filtered, provided 20 grams of a white solid. The 20 grams of crude product was recrystallized from hexane to yield 15.5 grams (42.6% yield) of product having a melting point of 44.5°–46° C. Infrared analysis confirmed the following structure:

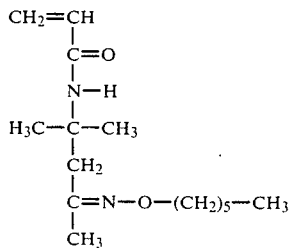

EXAMPLE 6

Preparation of the p-toluenesulfonyl carbamate derivative of diacetone acrylamide To a stirred solution of 36.4 grams (0.2 mole) of diacetone acrylamide oxime in 100 mls. of tetrahydrofuran at 25° C. were added 38.5 grams (0.2 mole) of p-toluenesulfonyl isocyanate dropwise over a 40-minute period. An exotherm was observed and the reaction temperature peaked at 40° C. Upon completion of the addition, the reaction mixture was heated for one additional hour at 40° C. Upon cooling, 500 mls. of diethyl ether were added and after refrigeration, 60 grams (80% yield) of yellowish crystals were isolated. The product was recrystallized twice from ethyl acetate providing white crystals (at about 35% yield) having a melting point of 117°–121° C. Thin layer chromatographic and nuclear magnetic resonance analytical techniques confirmed the following structure:

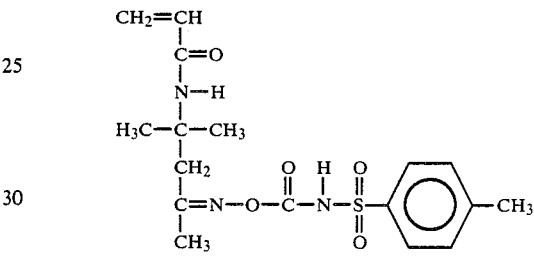

EXAMPLE 7

Preparation of poly(diacetone acrylamide oxime)

A solution in acetonitrile of 0.4514 gram of the poly(diacetone acrylamide oxime) and methylsulfonylethyl derivative, prepared as described in EXAMPLE 3—Part B, was stirred under nitrogen with a five-fold theoretical excess of 10% potassium hydroxide aqueous solution. The resulting solution, after one hour of stirring was neutralized at room temperature with dilute acetic acid (8.5 Normal) to a pH of 8. Deblocked polymer started to precipitate from solution in the 12.5 to 12.0 pH region. The polymer was separated, washed with distilled water and dried under vacuo at 55° C. to give 0.4048 gram of poly(diacetone acrylamide oxime). Structure of the polymer was confirmed by infrared and C13 NMR analytical techniques.

EXAMPLE 8

The procedure in EXAMPLE 7 was repeated except that 0.9878 gram of the derivative polymer was used and dilute hydrochloric acid (4N) was utilized in place of acetic acid. The result was the production of 0.6885 gram of the desired polymer, i.e., poly(diacetone acrylamide oxime).

What is claimed is:

1. A process for preparing a polymeric oxime which comprises polymerizing a polymerizable hydrogen-blocked derivative of an ethylenically unsaturated monomeric oxime to provide a polymer comprising recurring units from said polymerizable hydrogen-blocked derivative, said hydrogen-blocked derivative having the formula

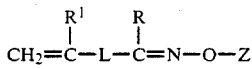

wherein R is hydrogen, lower alkyl, aryl, aralkyl or alkaryl, $R^1$ is hydrogen or lower alkyl, L is a divalent organic linking group and Z is a hydrogen-blocking group capable of being replaced by a hydrogen atom; and replacing hydrogen-blocking Z groups of said polymer with hydrogen atoms to provide a polymer containing oximino groups.

2. The process of claim 1 wherein said polymerizable hydrogen-blocked oxime derivative is a carbonate, carbamate, ester or ether derivative.

3. The process of claim 1 wherein said replacement of hydrogen-blocking Z groups with hydrogen atoms is effected by hydrolysis.

4. The process of claim 1 wherein the hydrogen-blocking Z group of said monomeric oxime derivative is a group

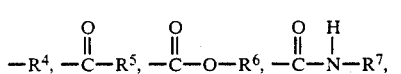

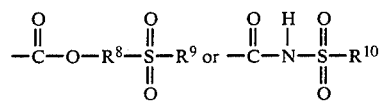

wherein $R^8$ is a divalent alkylene or arylene radical and each of $R^4$, $R^5$, $R^6$, $R^7$, $R^9$ and $R^{10}$ is alkyl, aryl, alkaryl, aralkyl, a carbocyclic radical or a 5- or 6-membered heterocyclic radical.

5. The process of claim 4 wherein the hydrogen-blocking Z group of said monomeric oxime derivative is a group

where $R^5$ is aryl or a group

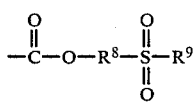

where $R^8$ is alkylene and $R^9$ is alkyl.

6. The process of claim 1 where said polymerization of said polymerizable hydrogen-blocked oxime derivative is effected by initiating polymerization with a redox or azo-type polymerization initiating agent.

7. The process of claim 1 wherein said divalent organic linking group is a group having the formula

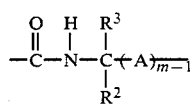

wherein each of $R^2$ and $R^3$ is independently hydrogen or lower alkyl, A is alkylene and m is an integer one or two.

8. The process of claim 1 wherein said polymerizable hydrogen-blocked oxime derivative is a monomer having the formula

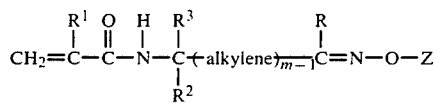

wherein R is hydrogen, lower alkyl, aryl, aralkyl or alkaryl; $R^1$ is hydrogen or lower alkyl; Z is a hydrogen-blocking group capable of being replaced by a hydrogen atom; $R^2$ and $R^3$ are each independently lower alkyl of from 1 to 6 carbon atoms; alkylene is an alkylene of from 1 to 8 carbon atoms; and m is an integer one or two.

9. The process of claim 8 wherein $R^1$ is hydrogen or methyl; each of $R^2$ and $R^3$ is methyl or ethyl; alkylene is methylene; and m is the integer two.

10. The process of claim 8 wherein said polymerizable hydrogen-blocked oxime derivative is a monomer having the formula

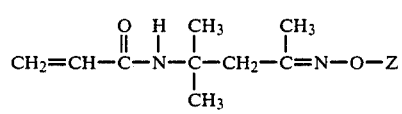

wherein Z is a hydrogen-blocking group capable of being replaced by a hydrogen atom.

11. The process of claim 10 wherein said hydrogen blocked oxime derivative is a carbonate, carbamate, ester or ether derivative.

12. The process of claim 10 wherein said hydrogen-blocking Z group is

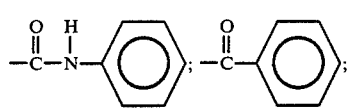

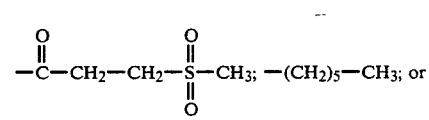

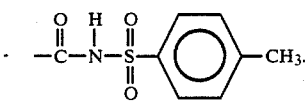

13. The process of claim 1 wherein said polymerizable hydrogen-blocked derivative is copolymerized with a copolymerizable ethylenically unsaturated comonomer.

14. The process of claim 13 wherein said copolymerizable ethylenically unsaturated comonomer is acrylic acid.

15. The process of claim 1 wherein said hydrogen-blocking Z groups of said polymer are replaced with hydrogen atoms by hydrolysis.

16. A process for preparing a polymeric oxime which comprises polymerizing a polymerizable hydrogen-blocked derivative of an ethylenically unsaturated monomeric oxime to provide a polymer comprising recurring units from said polymerizable hydrogen-blocked derivative, said hydrogen-blocked derivative having the formula

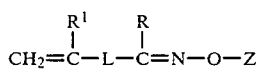

wherein R is hydrogen, lower alkyl, aryl, aralkyl or alkaryl, $R^1$ is hydrogen or lower alkyl, L is a divalent organic linking group having the formula

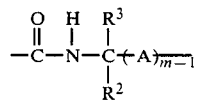

wherein each of $R^2$ and $R^3$ is independently hydrogen or lower alkyl, A is alkylene and m is an integer one or two, and Z is a hydrogen-blocking group

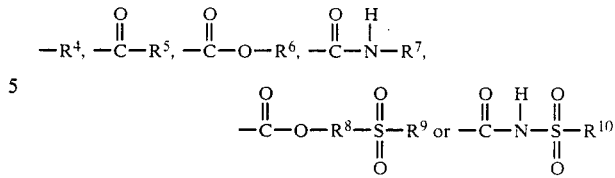

wherein $R^8$ is a divalent alkylene or arylene radical and each of $R^4$, $R^5$, $R^6$, $R^7$, $R^9$ and $R^{10}$ is alkyl, aryl, alkaryl, aralkyl, a carbocyclic radical or a 5- or 6-membered heterocyclic radical; and replacing hydrogen-blocking Z groups of said polymer with hydrogen atoms to provide a polymer containing oximino groups.

17. The process of claim 16 wherein said hydrogen-blocking Z groups of said polymer are replaced with hydrogen atoms by hydrolysis.

* * * * *